(12) United States Patent
Albert et al.

(10) Patent No.: US 11,471,051 B2
(45) Date of Patent: Oct. 18, 2022

(54) ULTRAVIOLET CARDIAC MONITORING AND ANALYSIS

(71) Applicant: AliveCor, Inc.

(72) Inventors: David E. Albert, Oklahoma City, OK (US); Bruce Satchwell, Gold Coast (AU)

(73) Assignee: AliveCor, Inc., Mountain View, CA (US)

( * ) Notice: Subject to any disclaimer, the term of this patent is extended or adjusted under 35 U.S.C. 154(b) by 0 days.

(21) Appl. No.: 16/889,438

(22) Filed: Jun. 1, 2020

(65) Prior Publication Data

US 2020/0375458 A1 Dec. 3, 2020

Related U.S. Application Data

(60) Provisional application No. 62/855,113, filed on May 31, 2019.

(51) Int. Cl.
*A61B 5/00* (2006.01)
*A61B 5/282* (2021.01)

(52) U.S. Cl.
CPC .......... *A61B 5/0006* (2013.01); *A61B 5/0022* (2013.01); *A61B 5/282* (2021.01);
(Continued)

(58) Field of Classification Search
None
See application file for complete search history.

(56) References Cited

U.S. PATENT DOCUMENTS

2010/0274329 A1* 10/2010 Bradley ............... A61N 1/328
607/90
2011/0015496 A1* 1/2011 Sherman ............. A61B 5/6898
600/301
(Continued)

OTHER PUBLICATIONS

Heartcheck Pen, The Heartcheck PEN handheld ECG Device, https://www.youtube.com/watch?v=Pk_dNPKmDD0, Nov. 23, 2012, viewed on May 21, 2021.*
(Continued)

*Primary Examiner* — Lynsey C Eiseman
*Assistant Examiner* — James Moss
(74) *Attorney, Agent, or Firm* — Womble Bond Dickinson (US) LLP

(57) ABSTRACT

A mobile electrocardiogram (ECG) device is described, comprising an electrode assembly comprising electrodes, wherein the electrode assembly senses heart-related signals when in contact with a body of a user, and produces electrical signals representing the sensed heart-related signals. The mobile ECG device further comprises a converter assembly electrically connected to the electrode assembly, configured to convert the electrical signals to a modulated signal, wherein the modulated signal carries the electrical signals representing the sensed heart-related signals. The mobile ECG device further comprises a transmitter that transmits the modulated signal wirelessly to a computing device. The mobile ECG device further comprises a light-emitting device to facilitate an optimal placement of the electrode on the body of the user. The mobile ECG device further comprises a housing containing the electrode assembly, the converter assembly, the transmitter, and the light-emitting device.

18 Claims, 7 Drawing Sheets

(52) U.S. Cl.
CPC ............ *A61B 5/6842* (2013.01); *A61B 5/742* (2013.01); *A61B 2560/0431* (2013.01); *A61B 2562/16* (2013.01)

(56) References Cited

U.S. PATENT DOCUMENTS

| | | | | |
|---|---|---|---|---|
| 2011/0301439 | A1* | 12/2011 | Albert | .................... H04B 11/00 600/301 |
| 2013/0245486 | A1* | 9/2013 | Simon | .................. A61B 5/4041 600/546 |
| 2014/0228665 | A1* | 8/2014 | Albert | .................. A61B 5/0245 600/384 |
| 2014/0364797 | A1* | 12/2014 | Schoenbach | ......... A61N 5/0625 606/41 |
| 2015/0230863 | A1* | 8/2015 | Youngquist | .......... A61B 18/203 606/9 |
| 2016/0296171 | A1* | 10/2016 | Drori | ................... A61B 5/4839 |
| 2017/0119307 | A1* | 5/2017 | Shim | .................... A61B 5/0022 |
| 2018/0289945 | A1* | 10/2018 | Lampo | ................ A61N 1/0484 |
| 2020/0066141 | A1* | 2/2020 | De Smet | ............. F21V 33/0052 |

OTHER PUBLICATIONS

Heartcheck Pen, PEN Instructional Hand Measurements, https://www.youtube.com/watch?v=Zj5jaEpmOMM, Jan. 14, 2013, viewed on May 21, 2021.*

Heartcheck Pen, PEN Instructional—Chest Measurementsts, https://www.youtube.com/watch?v=lfJU6QVtnHM, Jan. 14, 2013, viewed on May 21, 2021.*

Scott R. Haines et al. (2012) The Use of NearUltraviolet Light to Facilitate Pupil Examination in Patients with Dark Irides, Neuro-Ophthalmology, 36:3, 114-115, DOI: 10.3109/01658107.2012. 686144.*

* cited by examiner

ULTRAVIOLET CARDIAC MONITORING AND ANALYSIS

CROSS-REFERENCE TO RELATED APPLICATIONS

This application claims the benefit of U.S. Patent Provisional Application Ser. No. 62/855,113, filed May 31, 2019, the entirety of which is incorporated by reference herein.

BACKGROUND

It is estimated that by 2030, over 23 million people will die from cardiovascular diseases annually. Cardiovascular diseases are prevalent in the populations of high-income and low-income countries alike. Monitoring of cardiovascular function will aid in the treatment and prevention of cardiovascular disease.

The mammalian heart generates and conducts an electric current that signals and initiates the coordinated contraction of the heart. In humans, an electric signal is produced by a portion of the heart known as the SA node. After being generated by the SA node, the electric current travels throughout the myocardium in a manner that is predictable in a healthy heart.

In general, an electrocardiogram (ECG) is a graphic representation of the electric conduction of the heart over time as projected on the surface of the body. An ECG is typically displayed on a graph having an x and y axis. Typically, the x-axis of an ECG displays time and the Y-axis of an ECG displays the electric potential (in millivolts) of an electric current that is conducted through the heart during normal cardiac function.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
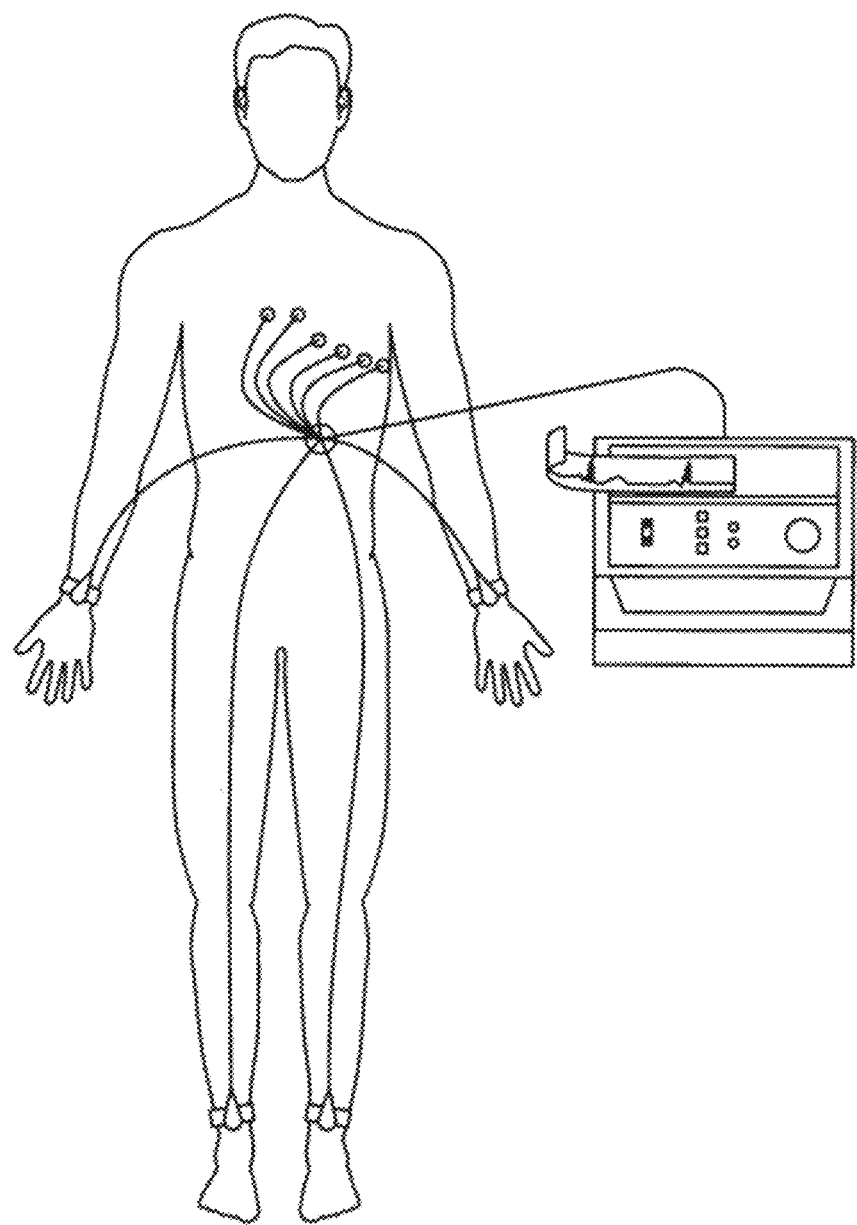
FIG. 1 is a pictorial representation of a prior art electrocardiograph having 10 electrodes positioned on a patient's body for taking a prior art 12-lead electrocardiogram.

Described herein are devices, methods, and systems for sensing, displaying, and analyzing an ECG of an individual with a light-emitting ECG device for optimal electrode placement. In one embodiment, as described herein, accurate electrode placement is critical to obtaining accurate electrocardiogram (ECG) measurements and analysis. Accurate electrode placement can be difficult, as a variety of electrodes should be placed in precise, predefined locations on a user's body for optimal results.

Advantageously, the embodiments described herein allow for those predefined locations on a user's body to be marked with invisible ink, either via a permanent or semi-permanent method (e.g., tattoo), or by some other more temporary means (e.g., washable or semi-permanent marker). With such invisible markings in place, a light (e.g., an ultraviolet (UV)) built into an ECG device may be used to guide a user's accurate placement of electrodes by shining the light over the user's body to reveal the otherwise invisible markings. Markings may be applied by a medical professional or by a user or other third-party with the help of a diagram, mobile application, or other guide.

In some embodiments of the systems, devices, and methods described herein, an ECG sensing device comprises a mobile computing device configured to sense one or more of ECG leads I, II, III, aVR, aVL, aVF, V1, V2, V3, V4, V5, and V6.

In some embodiments, systems, devices, and methods described herein, ECG sensing device comprises less than the ten electrodes of a traditional ECG sensing device. In some embodiments of the ECG sensing device, the device comprises two or more electrodes that are configured to sense one or more of ECG leads I, II, III, aVR, aVL, aVF, V1, V2, V3, V4, V5, and V6.

In some embodiments, an ECG sensing device as described herein senses six ECG leads, which are leads I, II, III, aVR, aVL, and aVF. In some embodiments, an ECG sensing device as described herein senses twelve ECG leads, which are I, II, III, aVR, aVL, aVF V1, V2, V3, V4, V5, and V6. An ECG sensing device as described herein comprising two or more electrodes may be configured to sense six leads or twelve leads.

Lead I is typically a waveform representing the electric potential difference between the left arm (LA) and the right arm (RA) as expressed by the relationship lead I=LA−RA.

Lead II is typically a waveform representing the electric potential difference between the right arm and left leg (LL) as expressed by the relationship lead II=LL−RA.

Lead III is typically a waveform representing the electric potential difference between the left leg and left arm as expressed by the relationship lead III=LL−LA.

Lead aVR is typically a waveform representing the electric potential difference between the right arm and a composite of the left arm and left leg as expressed by the relationship aVR=RA−½(LA+LL).

Lead aVL, is typically a waveform representing the electric potential difference between the left arm and a composite of the right arm and left leg as expressed by the relationship aVL=LA−½(RA+LL).

Lead aVF is typically a waveform representing the electric potential difference between the left leg and a composite of the left arm and right arm expressed by the relationship aVF=LL−½(LA+RA).

Leads aVR, aVL, and aVF are generated by an ECG sensing device or system from electric potential differences between one of RA, LA, and LL, and a composite comprising of two of RA, LA, and LL. Thus, three electrodes positioned at RA, LA, and LL will sense aVR, aVL, and aVF simultaneously based on the above relationships. Which is to say that while leads, I, II, and III each require input from only two electrodes, and aVR, aVL, and aVF may require input from three electrodes positioned at RA, LA, and LL.

A standard named composite pole is known as Wilson's Central Terminal (WCT). WCT may be expressed by the relationship WCT=⅓(RA+LA+LL).

Leads V1, V2, V3, V4, V5, and V6 are unipolar leads and as such each uses a position on the chest as its positive pole and WCT as its negative pole. The positions on the chest at which an electrode is placed for the purposes of measuring V1, V2, V3, V4, V5, and V6 are standardized with regard to a user's anatomy. The positive pole of V1 is typically measured in the fourth intercostal space just to the right of the sternum. The positive pole of V2 is typically measured in the fourth intercostal space just to the left of the sternum. The positive pole of V3 is typically measured between leads V2 and V4. The positive pole of V4 is typically measured in the fifth intercostal space in the mid-clavicular line. The positive pole of V5 is typically measured horizontally even with V4, in the left anterior axillary line. The positive pole of V6 is typically measured horizontally even with V4 and V5 in the midaxillary line.

In a three electrode ECG sensing device, RA serves as the reference electrode for lead I and lead II so that it can be taken to be zero (i.e. assumed to represent zero). As such, lead I can be expressed as lead I=LA−0 or lead I=LA and lead II can be expressed as lead II=LL−0 or lead II=LL.

Taking RA=0 in a three electrode ECG sensing device, WCT may be expressed as (lead I+lead II)/3.

Taking RA=0 in the three electrode ECG sensing device, aVR may be expressed as −(lead I lead II)/2, aVL=lead I−(lead II/2), and aVF may be expressed as lead II−(lead I/2).

In some embodiments of the ECG sensing device described herein, an ECG sensing device comprises a mobile computing device along with two or more electrodes.

FIG. 1 is a pictorial representation of the 10 electrodes of a conventional electrocardiograph being placed on the patient for obtaining a standard 12-lead ECG. The electrode placed on the right arm is commonly referred to as RA. The electrode placed on the left arm is referred to as LA. The RA and LA electrodes are placed at the same location on the left and right arms, preferably but not necessarily near the wrist. The leg electrodes can be referred to as RL for the right leg and LL for the left leg. The RL and LL electrodes are placed on the same location for the left and right legs, preferably but not necessarily near the ankle.

Figure 2:
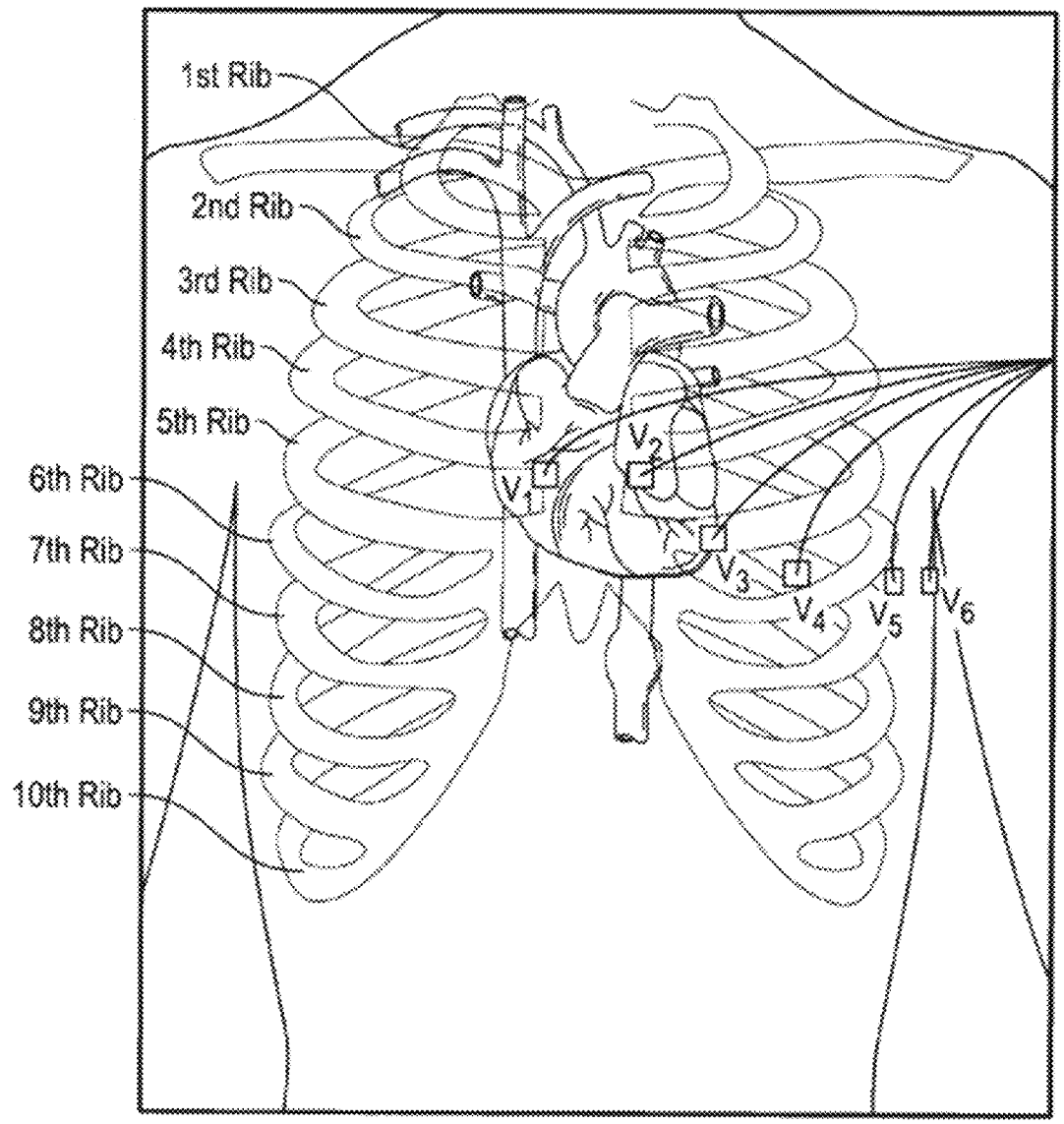
FIG. 2 is a pictorial representation of a chest showing an example of electrode placement on the chest for taking a prior art 12-lead electrocardiogram.

FIG. 2 illustrates the placement of the six electrodes on the chest with such electrodes being labeled $V_1$, $V_2$, $V_3$, $V_4$, $V_5$, and $V_6$. In one embodiment, the location of precordial leads $V_1$-$V_6$ may be marked with invisible markings, as described herein. Such markings may be performed on tyeh surface of a user's skin or sub-dermally by a doctor, by the user themselves, or with the help of any other third-party. $V_1$ is placed in the fourth intercostal space, for example between ribs 4 and 5, just to the right of the sternum. $V_2$ is placed in the fourth intercostal space, for example between ribs 4 and 5, just to the left of the sternum. $V_3$ is placed in the fifth intercostal space midway between electrodes $V_2$ and $V_4$. $V_4$ is placed in the fifth intercostal space between ribs 5 and 6 on the left mid-clavicular line. $V_5$ is placed horizontally even with $V_4$ on the left anterior axillary line. $V_6$ is placed horizontally even with $V_4$ and $V_5$ on the left mid-axillary line.

The electrocardiograph then calculates and outputs three limb lead waveforms. Limb leads I, II, and III are bipolar leads having one positive and one negative pole. Lead I is the voltage between the left arm (LA) and right arm (RA), e.g. I=LA−RA. Lead II is the voltage between the left leg (LL) and right arm (RA), e.g. II=LL−RA. Lead III is the voltage between the left leg (LL) and left arm (LA), e.g. III=LL−LA. Leads I, II and III are commonly referred to as "limb leads."

Unipolar leads also have two poles; however, the negative pole is a composite pole made up of signals from multiple other electrodes. In a conventional cardiograph for obtaining a 12-lead ECG, all leads except the limb leads are unipolar (aVR, aVL, aVF, $V_1$, $V_2$, $V_3$, $V_4$, $V_5$, and $V_6$). Augmented limb leads (aVR, aVL, and aVF) view the heart from different angles (or vectors) and are determined from RA, RL, LL, and LA. For example, the augmented vector right (aVR) positions the positive electrode on the right arm, while the negative electrode is a combination of the left arm electrode and the left leg electrode, which "augments" the signal strength of the positive electrode on the right arm. Thus the augmented vector right (aVR) is equal to RA−(LA+LL)/2 or −(I+II)/2. The augmented vector left (aVL) is equal to LA−(RA+LL)/2 or (I−II)/2. The augmented vector foot (aVF) is equal to LL−(RA+LA)/2 or (II−I)/2.

In one embodiment, the six electrodes on the chest of the patient are close enough to the heart that they do not require augmentation. A composite pole called Wilson's central terminal (often symbolized as $CT_W$, $V_W$, or WCT) is used as the negative terminal. Wilson's central terminal is produced by connecting the electrodes RA, LA, and LL together, via a simple resistive network, to give an average potential across the body, which approximates the potential at an infinite distance (i.e. zero). Wilson's central terminal, WCT, is calculated as (RA+LA+LL)/3.

Figure 3:
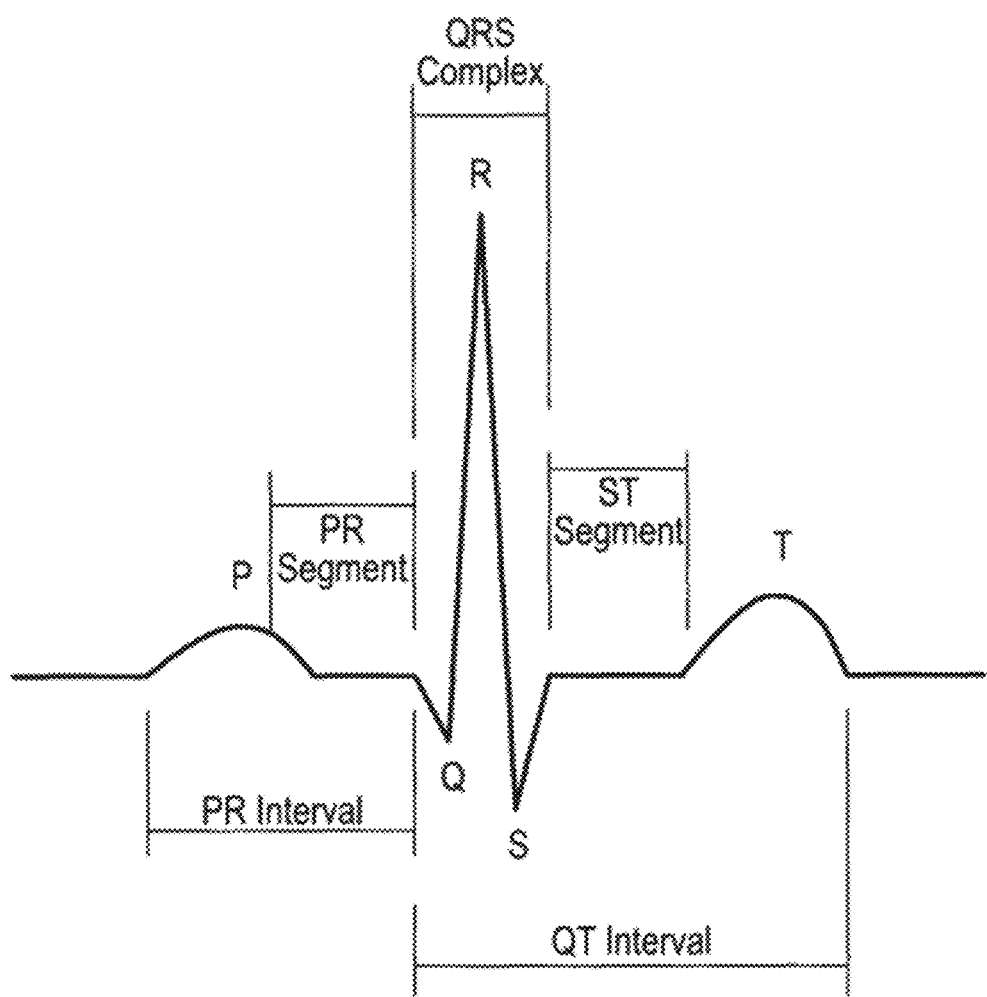
FIG. 3 illustrates an example Lead I annotated to show PQRST waves generated by a 12-lead electrocardiograph.
Figure 4:
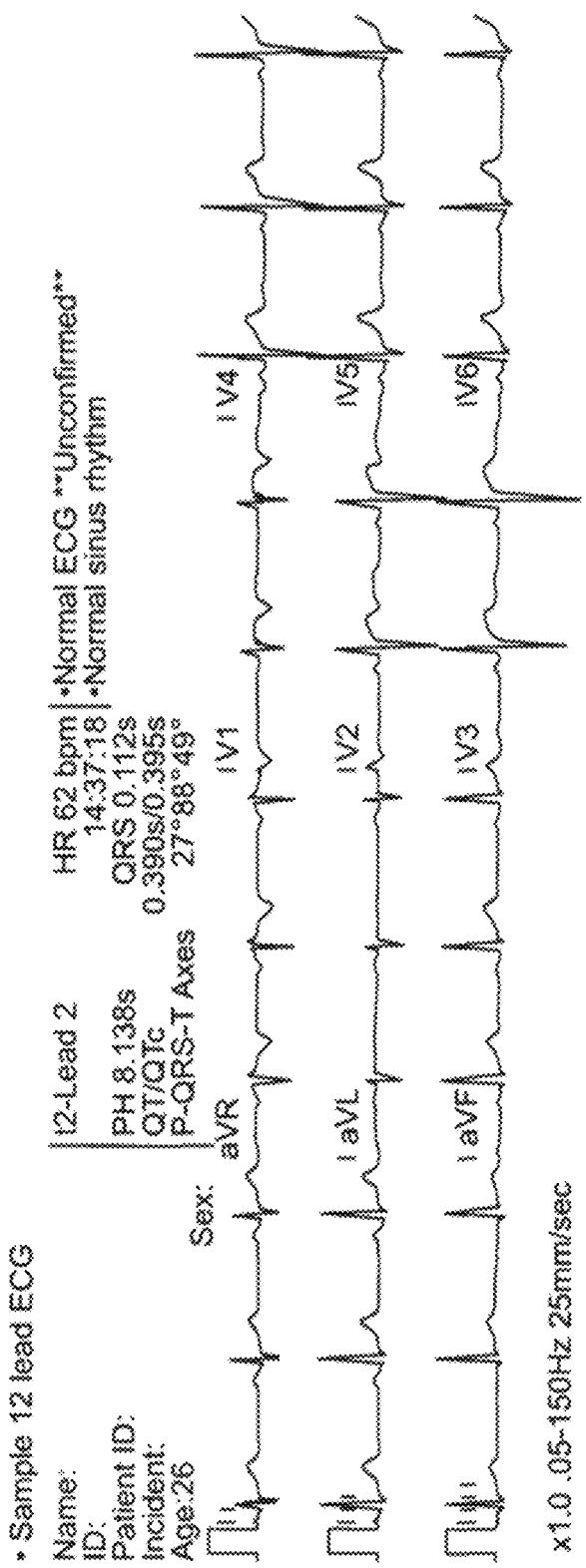
FIG. 4 shows an example 12-lead electrocardiogram in a conventional format.

FIG. 3 illustrates an example Lead I annotated to show PQRST waves generated by a 12-lead electrocardiograph. The identification and measurement of the PQRST waves based on the electrocardiogram is known in the art. FIG. 4 illustrates an example of a 12-lead electrocardiogram in a conventional format.

While a conventional 12-lead electrocardiogram gives very useful information concerning the health and condition of an individual's heart, the conventional electrocardiograph equipment is expensive and the procedure is not normally available in areas other than hospitals and medical doctors' offices. Therefore, monitoring is not done frequently even in wealthy countries, and in poorer areas of the world an electrocardiograph may not even be available.

FIG. 4 shows an example 12-lead electrocardiogram in a conventional format. The term "lead" in electrocardiography causes much confusion because it can be used to refer to two different things. In accordance with common usage, the word "lead" may be used to refer to the electrical cable attaching the electrodes to the electrocardiograph. Alternatively, and as used herein, the word "lead" refers to the tracing of the voltage difference between at least two electrodes. Conventionally, 10 electrodes are used to produce twelve of this type of lead, thereby forming a "12-lead" electrocardiogram as exemplified in FIG. 4.

Figure 5A:
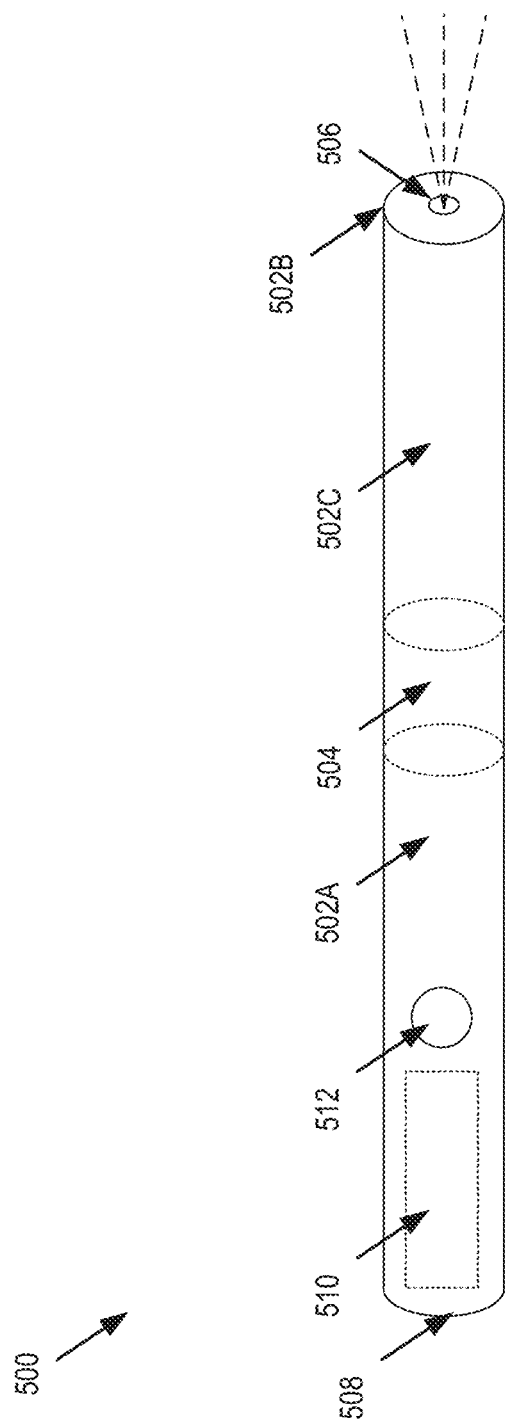
FIG. 5A shows an exemplary ECG sensing device having two electrodes and a light-emitting device, as described herein.

FIG. 5A shows an exemplary ECG sensing device 500 having two electrodes and a light-emitting device, as described herein. In some embodiments, one or more capacitive electrodes are used in the ECG sensing device 500 so that, for example, the capacitive electrode senses an electric potential through a garment worn over the body of the user or directly against a user's skin. Similarly, a conductive spray or gel may be placed on the body of the user so that a typical electrode senses an electric potential through a garment worn over the body of the user.

In one embodiment, the ECG sensing device 500 is shaped like a flashlight (e.g., a penlight), although any other form factor is contemplated. In other words, the ECG sensing device 500 may be a cylinder having two ends. In one embodiment, the device 500 may be approximately three to six inches long, and approximately one half inch to one and a half inches in diameter. In a variety of other embodiments, any other suitable dimensions may be used. In one embodiment, the ECG sensing device 500 is constructed, in whole or in part, from stainless steel or some other suitable material. In one embodiment, the ECG device 500 includes an exterior coating, such as Titanium Nitride or other suitable coating. Advantageously, such materials may increase biocompatibility and optimum electrode characteristics.

In one embodiment, device 500 is referred to as a mobile computing device herein, and includes all necessary components to sense, record, and display ECG signals and analysis. In another embodiment, device 500 connects via wires or wirelessly to a separate mobile computing device. In such a case, the device 500 may sense the ECG signals and send the unmodified or modified signals to a mobile computing device for further analysis and/or display. In yet another embodiment, any combination of the two examples listed above is possible. For example, although the device 500 may be considered a self-contained mobile computing device, capable of performing all operations described herein, device 500 may still connect to, and interact with, a second mobile computing device for any suitable purpose (offloading processing/analysis, display, etc.).

The device 500 may include one or more controls and/or indicators. For example, the device 500 may include buttons, dials, etc. to select functions (e.g., turning on/off ECG reading, to begin to transmit ECG information, etc.). The device 500 may further include a display that displays a recorded ECG.

In one embodiment, device 500 includes two electrodes 502A (e.g., located on a side of device 500) and 502B (e.g., located on an end of device 500). In another embodiment, device 500 includes a third electrode 502C (e.g., located on a side of device 500). The electrodes 502 may be insulated from each other via dielectrics (e.g., 504) or other suitable materials such that they are able to sense and record distinct signals. In one embodiment, the electrodes 502 are silver-silver chloride (or any other suitable material) electrodes. In one embodiment, the electrodes 502A and 502C wrap around the circumference of the device 500, as shown. In another embodiment, the electrodes 502A and 502C are localized to only portions of the areas shown on device 500. In one embodiment, the electrode 502B forms a ring around one end of the device 500, wrapping around the circumference of the device 500. Advantageously, a user may make contact with electrodes 502A and 502C using one or more hands/fingers, while pressing the electrode 502B against a body part (e.g., a leg or chest). As such, three separate and distinct signals may be sensed simultaneously from three separate and distinct body parts to record two leads simultaneously.

In one embodiment, the device 500 may include a light emitting device 506 (e.g., one or more LED devices) on one end (e.g., the end collocated with the electrode 502B) and a hole through the end of the device 500 to permit light from the light emitting device 506 to pass through the end of the device 500. Light emitting device 506 may emit any frequency of light, including ultraviolet light (UV). Light emitting device 506 may include multiple light emitters, and a user may be permitted to select the type of light to be emitted. Advantageously, by emitting ultraviolet light, a user may use light emitting device 506 to locate ultraviolet-sensitive markings on his or her body. The markings may include UV-sensitive ink or dye (e.g., in the form of a tattoo or some other more-temporary medium—from a marker, for example). Once located, the end of the device 500 that includes the light emitting device 506 and electrode 502B may be accurately pressed directly on top of the marking, thus ensuring that electrode 502B makes contact with the body of the user in an area that most provides for an accurate sensing of an ECG signal.

In another embodiment, device may include, on the same end as the light emitting device or the opposite end (e.g., 508), a hole to allow the extrusion of a conductive material (e.g., gel/liquid). In such an embodiment, device 500 may include an internal container or bladder 510 for the storage of such conductive material, and a button 512 or other suitable device to activate the extrusion. In various embodiments, the device 500 may include one or both of the light emitting device 506, the hole to allow for the extrusion of the conductive material, or neither.

In another embodiment, device 500 may include an electrode connector (e.g., female socket) on one end or a side allowing one or more ECG electrodes to be connected to the device 500 to be used on skin with an adhesive or without an adhesive (e.g., only a conductive gel and the electrodes).

In one practical example, a user is sitting in a chair and holds the device with one or both hands so that each hand contacts just one electrode on the device 500. The end of the device 500 that includes the light emitting device 506 is scanned over the user's leg, to locate an ultraviolet marking on the leg. Once found, the device 500 is held against the user's leg, directly on the located marking, so that an electrode (e.g., electrode 502B) is pressed against the left leg of the user.

The device 500 (with, optionally, a separate mobile computing device) may then be used to record Lead I, Lead II, and Lead III, from which at least three additional leads may be determined, as described herein. Specifically, the augmented leads, aVR, aVL, and aVF, may be determined using Leads I, II, and III.

While not shown in FIG. 5A, an individual may also record the precordial leads V1, V2, V3, V4, V5, and V6 using a three electrode ECG sensing device 500 as described herein. The device 500 may be configured so that an individual holds an electrode (e.g., 502A, 502C) with one of each of his left and right hands and holds the third electrode (e.g., 502B) sequentially against the six electrode positions on the chest described herein corresponding to leads V1, V2, V3, V4, V5, and V6. In some embodiments, while the user holds an electrode (e.g., 502A, 502C) of the device 500 with each of his right and left hands and simultaneously holds the third electrode (e.g., 502B) of the device 500 against a positon on his chest corresponding to V1, V2, V3, V4, V5, and V6, each of the electric potentials sensed at the chest positions corresponding to V1, V2, V3, V4, V5, and V6 are sensed simultaneously with an electric potential sensed at LA and RA. Lead I is equivalent to the potential difference between LA and RA. Thus, in some embodiments, measuring an electric potential at a position on the chest corresponding to any of V1, V2, V3, V4, V5, and V6 together with the electric potential at the LA and RA positions is equivalent to the difference in potential at the chest position and lead I. That is, for example, using all three electrodes of device 500 as described, V1 (the electric potential at the V1 chest position)=("CP1")−WCT (WCT=(RA+LA+LL)/3 or (lead I+lead II)/3).

In some embodiments, the six precordial chest positions may be represented as ("CP1," "CP2," "CP3," "CP4," "CP5," and "CP6") and a composite value may be known as Wilson's Central Terminal ("WCT").

"CP(x)" corresponds to any of the six potentials sensed at the anatomical precordial lead positions (where "x" is a position number 1-6). For example, CP1 is the ECG measurement sensed at a location at which an electrode is placed to measure V1, and that position is approximately in the second intercostal space immediately to the right of the sternum. Thus, lead V1=CP1−WCT.

WCT is equal to one third of the sum of the potentials sensed at the right upper extremity, left upper extremity, and left lower leg or ⅓(RA+LA+LL). In a standard ECG that uses ten simultaneously placed electrodes, a WCT value is generated at the same time that a precordial lead is sensed, because RA, LA, LL, which determine WCT, are sensed at the same time as CPI, CP2, CP3, CP4, CP5, and CP6.

An ECG sensing device 500 as described herein comprises at least two electrodes and less than the ten standard electrodes. In some embodiments of the ECG sensing device described herein, the device comprises three electrodes. In these embodiments, the electrodes are positioned and configured to simultaneously sense the six limb leads I, II, III, aVR, aVL, and aVF when a user contacts a first electrode with a right upper extremity, a second electrode with a left upper extremity, and a third electrode with a left lower extremity.

As also described herein, an ECG sensing device 500 is configured to sense the six leads V1, V2, V3, V4, V5, and V6 sequentially when a user, for example, contacts a first electrode with a right upper extremity, a second electrode with a left upper extremity, and a third electrode with an area of his or her chest corresponding to a precordial lead position.

In some embodiments of the ECG sensing device comprising three electrodes described herein, RA, LA, LL, which determine WCT, are not sensed simultaneously with one or more precordial leads. That is, when one of the three electrodes of the ECG sensing device is held against the chest wall of a user, only two electrodes remain free and a traditional WCT cannot be simultaneously determined. In some of these embodiments, RA is set to 0. When RA=0, it provides a WCT=(0+LA+LL)/3 or ((LA−0)+(LL−0))/3 which can be further expressed as WCT=(lead I+lead II)/3.

Likewise, in these embodiments, wherein RA is set to 0, an averaged WCT=(averaged lead I+averaged lead II)/3. An averaged WCT in some embodiments is generated using an averaged lead I and an averaged lead II that are generated using, for example, an ensemble averaging method on the lead I and lead II waveforms sensed by the ECG sensing device described herein. Generating an average WCT is beneficial in, for example, signal filtering and also simplifies alignment of values for purposes of subtraction. That is, in some embodiments, CPI, CP2, CP3, CP4, CP5, and CP6 are each averaged and an averaged WCT is respectively subtracted from each to generate V1, V2, V3, V4, V5, and V6.

In this manner, a three lead ECG sensing device 500 is used to sense a 12-lead ECG. In a first step an individual holds a first electrode (e.g., 502A) with a left hand a second electrode (e.g., 502C) with a right hand and presses a third electrode (e.g., 502B) against their left leg to simultaneously generate leads I, II, III, aVR, aVL, and aVF. In a second step the user holds a first electrode (e.g., 502A) with a left hand, a second electrode (e.g., 502C) with a right hand, and a third electrode (e.g., 502B) against the six precordial lead positions in order to sense leads V1, V2, V3, V4, V5, and V6.

In some embodiments, a software program on the ECG sensing device 500 or another mobile computing device displays or otherwise transmits instructions to an individual instructing the user as to how to position the electrode over the standard precordial lead chest positions. For example, a display may show an image of a location on the user's chest against which the user is instructed to hold the third electrode (e.g., 502B) while holding electrodes one and two (e.g., 502A, 502C) with his left and right hands respectively. In some embodiments, as described herein, such positioning may be aided by the use of the light emitting device 506 and markings (e.g., ultraviolet) on the body of the user. In some embodiments, the markings may be numbered or otherwise identified, so that a user may easily compare on-screen instructions with marked positions on their body.

In some embodiments, software on the ECG sensing device 500 or a separate computing device is configured to recognize if a first electrode is contacted by a left hand and second electrode is being contacted by a right hand versus whether a first electrode is contacted by a right hand a second electrode is contacted by a left hand. For example, in some embodiments, a third electrode is positioned on a different surface of the ECG sensing device 500 than the first and second electrodes, such that a user will likely need to swap hand positions to contact the precordial lead positions on their chest with the third electrode after contacting their left leg with the third electrode. In some embodiments, software on the ECG sensing device 500 or other mobile computing device receives information from a sensor coupled with or integrated with an ECG sensing device 500, wherein the sensor provides information about the position of the device in space. Examples of the class of sensors that sense such information include but are not limited to accelerometers, inclinometers, and gyrometers.

In some embodiments, the ECG sensing device 500 is configured to sense an ECG when one or more of the sensors are not engaged by the user. For example, in some embodiments, an ECG sensing device 500 comprises three electrodes, and the ECG sensing device 500 is configured to sense an ECG when either all three electrodes are engaged by the user or when any two of the three electrodes are engaged by the user. That is, in this embodiment, when a user, for example, contacts a skin surface on their right upper extremity with a first electrode and contacts a skin surface on their left upper extremity with a second electrode, but does not contact the third electrode, the ECG sensing device senses an ECG. When, in this example, the two of three electrodes are contacted by a right and left upper extremity respectively, a lead I is sensed. Likewise, when the two of three electrodes are contacted by a right upper extremity and left lower extremity respectively, a lead II is sensed. Likewise, when the two of three electrodes are contacted by a left upper extremity and left lower extremity respectively, a lead III is sensed. In this embodiment, the ECG sensing device 500 recognizes that one or more of the electrodes have not been contacted by a user while two or more electrodes have been contacted by the user, by, for example, sensing an electrode potential from two or more electrodes that are contacted but not sensing an electrode potential from electrodes that are not contacted by the user.

Figure 5B:
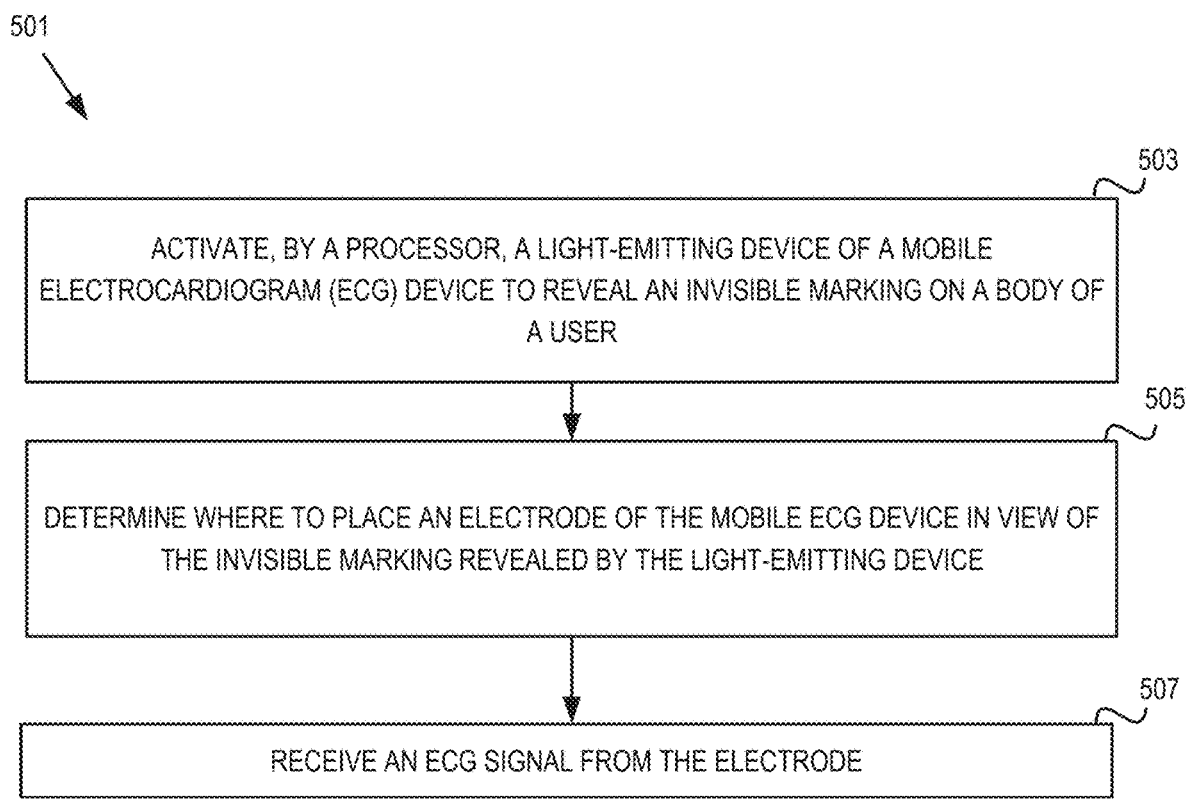
FIG. 5B shows an exemplary method of an ECG sensing device having two electrodes and a light-emitting device, as described herein.

FIG. 5B shows an exemplary method 501 of an ECG sensing device having two electrodes and a light-emitting device, as described herein. The method 501 may be performed by processing logic that comprises hardware (e.g., circuitry, dedicated logic, programmable logic, microcode, etc.), software (e.g., instructions run on a processing device to perform hardware simulation), or a combination thereof.

In embodiments, aspects of method 501 may be performed by the mobile ECG sensor/device/system of FIGS. 1-5A and FIG. 6.

With reference to FIG. 5B, method 501 illustrates example functions used by various embodiments. Although specific function blocks ("blocks") are disclosed in method 501, such blocks are merely examples. That is, embodiments are well suited to performing various other blocks or variations of the blocks recited in method 501. It is appreciated that the blocks in method 501 may be performed in an order different than presented, and that not all of the blocks in method 501 may be performed.

Referring to FIG. 5B, at block 503, processing logic may activate, by a processor, a light-emitting device of a mobile electrocardiogram (ECG) device to reveal an invisible marking on a body of a user. In one embodiment, the light-emitting device may include an ultraviolet light-emitter. In another embodiment, a light-emitting device emitting light of any other non-visible light spectrum may, be used. In one embodiment, the mobile ECG device includes or consists of a penlight form factor.

In one embodiment, the invisible marking on the body of the user corresponds to one or more precordial lead locations (e.g., V1-V6) on the body of the user. The invisible (e.g., to the unaided human eye) markings may include a variety of forms. For example, in one embodiment, the invisible marking comprises a tattoo (e.g., a permanent or semi-permanent marking) of invisible ink. In another embodiment, temporary marking (e.g., made by a marker, pen, temporary tattoo, etc.) of invisible ink.

At block 505, it may be determined where to place an electrode of the mobile ECG device in view of (e.g., based on) the invisible marking revealed by the light-emitting device and, at block 507, processing logic may receive an ECG signal from the electrode (e.g., placed on the invisible marking).

In some embodiments of the ECG sensing devices described herein, exemplary embodiments of which are shown in FIGS. 1-6, a mobile computing device is configured to run a software application as described herein. In further embodiments, the mobile computing device includes one or more hardware central processing units (CPUs) or general purpose graphics processing units (GPGPUs) that carry out the device's functions. In still further embodiments, the mobile computing device further comprises an operating system configured to perform executable instructions. In some embodiments, the mobile computing device is optionally connected a computer network. In further embodiments, the mobile computing device is optionally connected to the Internet such that it accesses the World Wide Web. In still further embodiments, the mobile computing device is optionally connected to a cloud computing infrastructure. In other embodiments, the mobile computing device is optionally connected to an intranet. In other embodiments, the mobile computing device is optionally connected to a data storage device.

In accordance with the description herein, suitable mobile computing devices include, by way of non-limiting examples, server computers, desktop computers, laptop computers, notebook computers, sub-notebook computers, netbook computers, netpad computers, handheld computers, smartphone, smartwatches, digital wearable devices, and tablet computers.

In some embodiments, the mobile computing device includes an operating system configured to perform executable instructions. The operating system is, for example, software, including programs and data, which manages the device's hardware and provides services for execution of applications. Non-limiting examples of suitable operating systems include FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

In some embodiments, a mobile computing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the mobile computing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes, optical disk drives, and cloud computing based storage. In further embodiments, the storage and/or memory device is a combination of devices such as those disclosed herein.

In some embodiments, the mobile computing device includes a display to send visual information to a user. In some embodiments, the mobile computing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In still further embodiments, the input device is a combination of devices such as those disclosed herein.

In various embodiments, the platforms, systems, media, and methods described herein include a cloud computing environment. In some embodiments, a cloud computing environment comprises a plurality of computing processors.

It should be understood that FIGS. 1-6 show exemplary embodiments of the user matter described herein, and, generally, numerous electrode positions, shapes, and sizes may be used in the devices described herein so that an individual comfortably and naturally contacts the electrodes. For example, all three electrodes may be positioned entirely on the sides of a computing device or a device cover.

In any of the embodiments shown in FIGS. 1-6, one or more electrodes may be configured to be removable from the ECG sensing device. In these embodiments the ECG sensing device has, for example, either a male or female connector configured to snap-fit couple to a corresponding male or female connector on a removable electrode.

While the embodiments of FIGS. 1-6 show ECG sensing devices comprising three electrodes, it should be understood that the other numbers of ECG electrodes may be incorporated into the ECG sensing devices described herein.

In general, any of the techniques, components and/or subsystems described above may be use or combined with any of the other examples. For example, any of the ECG devices described herein may include any of the features mentioned above.

All of the devices described herein are suitable for use in various systems, which may include one or more servers, one or more sensors, an electronic data communication networks, as well as other ECG sensing devices. In some embodiments, a plurality of ECG sensing devices as described herein transmit ECG data to one or more remote servers through an electronic data communication network. In some embodiments, the ECG data is analyzed using the one or more remote servers. In some embodiments, arrhythmia detection is carried out using a remote server that analyzes received ECG data.

All of the devices and systems described herein may also include one or more software modules. In some embodiments, software comprises an app that is configured to run on a mobile computing device such as, for example, a smartphone, a smartwatch, or a tablet computer. The software receives and processes ECG data received from an ECG sensing device. The software identifies separate leads within the transmitted data, based on for example, which electrodes the ECG data originated from. For example, the software may be able to identify a lead I based on the signal originating from two electrodes that measure an electric potential difference between the right and left upper extremities. Once an ECG is identified, the software may further be configured to display a single or multi-lead ECG on a display screen of a mobile computing device. The software may be configured to display six leads I, II, III, aVR, aVL, and aVF simultaneously on a display screen. The software may be configured to display one or more of the six leads I, II, III, aVR, aVL, and aVF on a display screen at once, wherein a user is able to manually toggle screens to see a different lead or leads on different toggled screens.

The software modules described herein comprise computer readable and executable code. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In a standard ECG waveform tracing, twelve ECG leads are displayed individually on an X and Y axis, wherein the Y-axis represents time and the X-axis represents voltage. In these tracings, all twelve ECG waveforms are aligned with respect to their X-axes. That is, the PQRST waveforms of all the leads all occur at the same time along the X-axis of each of the respective tracings. For example, in a traditional ECG waveform tracing, if a QRS complex occurs at 1 second on the X-axis in the lead I waveform tracing, a QRS complex occurs at 1 second in each of the other eleven ECG waveforms (i.e. leads II, III, aVR, aVL, aVF, V1, V2, V3, V4, V5, and V6).

The standard time aligned format allows health care providers to more easily obtain information from the twelve sensed ECG waveforms. In the traditional ECG tracing, time alignment is facilitated by virtue of the waveforms being sensed simultaneously by the ten electrodes of the traditional ECG that are all simultaneously positioned on the skin of the individual whose ECG is sensed. That is, because all twelve ECG leads of a traditional ECG are sensed simultaneously, time-alignment is achieved by simply displaying all of the waveforms together on identical axes.

Typically, an ECG of a normal beating heart has a predictable wave-form in each of the twelve ECG leads. A typical ECG wave-form comprises a number of component parts or sections. The components of a typical ECG waveform are referred to as P wave 812, QRS wave (or complex) 814, and T wave 816. Each wave or a complex of multiple waves (i.e. the QRS complex) is associated with a different phase of the hearts depolarization and repolarization. ECG portions between two waves are referred to as segments and ECG portions between more than two waves are referred to as intervals. For example, the ECG portion between the end of the S wave (part of QRS complex) and the beginning of the T wave 816 is referred to as the ST segment. For example, the portion of the ECG between the beginning of the Q wave (part of QRS complex) and the end of the T wave 816 is referred to as the QT interval.

An ECG is generated by measuring electric potentials on different skin surfaces of the body of an individual using electrodes. Typically, a single ECG recording or lead corresponds to a difference in electric potential between two points on the body of an individual measured over time.

In some embodiments of the systems, methods, and devices described herein, two or more sensed leads that are not simultaneously sensed are time aligned to generate a time aligned ECG tracing displaying two or more leads in a time aligned format such as in a traditional standard twelve lead ECG tracing. In some embodiments of the ECG sensing device described herein, one or more ECG sensing electrodes are not simultaneously positioned on the skin of the individual whose ECG is sensed (i.e. some leads may be sequentially sensed). For example, the limb leads (I, II, III, aVR, aVL, and aVF) are simultaneously sensed while one or more of the precordial leads are sensed separately from the limb leads. As such, in these embodiments, the six limb leads are not automatically time aligned with the individually and separately sensed precordial leads and a further process is carried out by a software application to time align one or more of the limb leads with one or more of the precordial leads. In some embodiments, one or more of the six precordial leads are individually sensed so that the individually sensed precordial leads are time aligned by a software application with the six limb leads as well as with the other precordial leads. In some embodiments, a software application described herein aligns two or more sensed precordial leads with one another and separately time aligns six sensed limb leads so that two sets of six leads are respectively time aligned (i.e. six time aligned precordial leads and six separately time aligned limb leads). In some embodiments, the software described herein aligns two or more sensed precordial leads with one another as well as with sensed limb leads so that all twelve sensed leads are time aligned.

In some embodiments of the devices, systems, and methods described herein, one or more average or median waveforms are generated for a first and a second lead so that waveforms corresponding to different heartbeats are time aligned. That is, in some embodiments wherein one or more leads are not sensed concurrently, an average or median waveform is generated for one or more of these leads and the averaged or median waveforms are time-aligned so that the PQRST waveforms are aligned vertically along the X-axis.

Time alignment of an ECG sensed with an ECG sensing device as described herein involves use of a software application that is configured to time align the PQRST waveforms of each lead sensed by an ECG sensing device so that the sensed ECG leads are aligned when displayed as are the waveforms in a traditional ECG tracing. In some embodiments of the ECG sensing device, the ECG sensing device comprises a software application configured to time align two or more sensed ECG leads. In some embodiments of the ECG sensing device, a software application configured to time align two or more sensed ECG leads is a component of a system that receives data from an ECG sensing device.

When first and second electrodes of the ECG sensing device described herein are contacted by the right and left upper extremities of the user at the same time that a third electrode of the device contacts any one of the six precordial lead positions, a lead I is sensed simultaneously along with a sensed precordial lead. That is, lead I is equal to a voltage sensed at the left upper extremity minus a voltage sensed at the right upper extremity, so when left upper extremity, right upper extremity, and chest are all respectively contacted by an electrode of the ECG sensing device described herein, a lead I is sensed in addition to a precordial lead. Therefore, when all six precordial leads are sensed sequentially, six respectively corresponding "precordial lead I recordings" are also generated: V1-lead I, V2-lead I, V3-lead I, V4-lead I, V5-lead I, and V6-lead I. Each of these six precordial lead I recordings is used to time align each of the precordial leads to the limb leads and thus time aligns precordial leads.

In some embodiments of the software application described herein, the software application aligns the precordial leads V1, V2, V3, V4, V5, and V6 by taking advantage of there being precordial lead I recordings sensed simultaneously with each of the V1, V2, V3, V4, V5, and V6 waveforms. That is, the precordial lead I recordings V1-lead I, V2-lead I, V3-lead I, V4-lead I, V5-lead I, and V6-lead I are each respectively time aligned with a precordial lead recording with which they are simultaneously sensed. Each of the precordial lead I recordings is time aligned with the lead I that is sensed along with the limb leads, by, for example, moving the precordial lead I recording a certain distance along the Y-axis, and because each of the precordial lead I recordings is time aligned with a precordial lead, each of the respective precordial leads V1, V2, V3, V4, V5, and V6 will also be time aligned when moved the same distance along the Y-axis as their co-sensed precordial lead I recording. For example, "V1-lead I" is a lead I recording that is time aligned with V1. "V1-lead I" is not the same as "lead I," which is the lead I recorded simultaneously sensed with the other five limb leads using the ECG sensing device described herein. "V1-lead I" is also not necessarily time aligned with "lead I" as these two different lead I recordings are not typically sensed simultaneously using the ECG sensing device described herein. Because, however, "V1-lead I" and "lead I" are both lead I recordings, they can be time aligned in a fairly straightforward manner as they would both be expected, when averaged, to have very similar (if not identical) morphology and timing between waveforms. For example, if the peak of the R wave of an averaged "lead I" occurs at 1 second, and the peak of the R wave of an averaged "V1-lead I" occurs at 1.5 seconds, the averaged "V1-lead I" will be re-positioned or shifted 0.5 seconds along the Y-axis so that the peak of its R wave occurs at 1 second as it does in in the averaged "lead I" Because V1 is time aligned with V1-lead I, it too must be shifted 0.5 seconds along the Y-axis in order to time align it with the averaged "lead I." When V1 is time aligned with "lead I," it will also be time aligned with the other five limb leads that are already time aligned with "lead I." A similar alignment occurs with V2, V3, V4, V5, and V6 by respectively aligning V2-lead I, V3-lead I, V4-lead I, V5-lead I, and V6-lead I with "lead I."

An exemplary time alignment method is as follows: The value of RA which is sensed at the right upper extremity may be set to 0 at any step within the following exemplary process. In a first step, the six limb leads are sensed as described herein when a user contacts a first electrode with a right upper extremity, a second electrode with a left upper extremity, and a third electrode with a left lower extremity. In this first step, the six sensed limb leads I, II, III, aVR, aVL, and aVF are time aligned by virtue of being sensed simultaneously. In a second step, the precordial leads are sensed sequentially as described herein wherein a first electrode of the device contacts a right upper extremity, a second electrode of the device contacts a left upper extremity, and a third electrode of the device sequentially contacts each of the six precordial chest positions CP1, CP2, C3, C4, CP5, and CP6. In a fourth step, the limb leads are averaged and as described (lead $I_{Average}$+lead $II_{Average}$)/3 generates a $WCT_{Average}$. In a third step, the electric potentials respectively sensed at CP1, CP2, CP3, CP4, CP5, and CP6 are each averaged. In a fourth step, $WCT_{Average}$ is used to generate the precordial lead values V1, V2, V3, V4, V5, and V6, as described, by subtracting $WCT_{Average}$ from each of the averaged electric potentials sensed at CP1, CP2, CP3, CP4, CP5, and CP6. In a fifth step, the precordial lead I recordings are each averaged. In a sixth step, the average precordial lead I recordings are each used to time align each of their respective co-sensed precordial leads V1, V2, V3, V4, V5, and V6 with lead $I_{Average}$. While in this exemplary method, the time alignment process is described as a series of steps, it should be understood that the steps described do not necessarily occur sequentially as at least some steps may occur in parallel nor do they necessarily occur in the order in which is described herein as at least some of the steps may occur in a different order. Likewise, it should be understood that one or more steps may be omitted or modified while still achieving the end point of the method which is a time alignment of one or more ECG leads sensed with an ECG sensing device as described herein. Thus, aligning any one of the precordial lead I recordings with lead $I_{Average}$ will provide an alignment of the associated precordial lead.

In some embodiments, an ECG sensing system comprises three electrodes coupled with a mobile computing device. The electrodes may be directly integrated into the mobile computing device. For example, the electrodes may be directly embedded in the housing of a mobile computing device such as, for example, a penlight. That is, electrodes may be components of a mobile device such as, for example, a penlight, a smartphone, a tablet computer, or a laptop computer. In this embodiment, ECG sensing electrodes are directly incorporated into the housing of a mobile computing device, and may, for example, be directly coupled, through a hardwire connection, to the hardware of the mobile computing device. For example, a processor may be directly hardwired to ECG sensing electrodes that are embedded within the housing of the device.

In some embodiments, one or more electrodes may be external to the mobile computing device. In such an embodiment, the one or more external electrodes are wirelessly or hardwire coupled to a mobile computing device. Non-limiting examples of wireless connections may comprise, for example, a WiFi connection between the one or more external electrodes and the device, a Bluetooth® connection between the one or more external electrodes and the device, a low power Bluetooth® connection between the one or more external electrodes and the device, an NFC (near field communication) connection between the one or more external electrodes and the device, or a near field ultrasound communication connection between the one or more external electrodes and the device. It should be understood by those having knowledge in the art that other means of communicating wirelessly with a device are suitable for use with the systems, devices, and methods described herein.

ECG sensing electrodes sense an ECG signal by measuring an electric potential difference between two points on the skin surface of an individual. When a first electrode is in contact with a right hand of an individual and a second electrode is in contact with a left hand of an individual, a lead I recording may be generated, which comprises a graphic representation of an electric potential difference between the right and left hands over time. When a third electrode is added to the electrodes that respectively contact the right and left hands, the remaining five limb leads may be generated. For example, in an ECG sensing device with three electrodes, the first electrode is configured to contact a right hand, the second electrode is configured to contact a left hand, and a third electrode is configured to contact a left leg. When all three electrodes of the ECG sensing device are contacted at once, a lead I, a lead II, and a lead III are generated. Lead I is the potential difference between the electrode in contact with the left hand and the electrode in contact with the right hand. Lead II is the potential difference between the electrode in contact with left leg and the electrode in contact with the right arm. Lead III is the potential difference between the electrode in contact with the left leg and the electrode in contact with the left arm. Simultaneously, unipolar leads aVR, aVL, and aVF may be determined using the recorded leads I, II, and III as described above. Thus, using only three electrodes as described herein, all six of the limb leads may be generated.

In some embodiments, an ECG sensing device comprises three electrodes that are placed so as to conveniently contact a particular portion of the skin surface of an individual. For example, one electrode is positioned to contact the right hand of an individual, one electrode is positioned to contact the left hand of an individual, and a third electrode is positioned to contact the left leg of an individual.

Additionally, software incorporated with any of the systems, devices, methods described herein may be configured to analyze ECG data received from an ECG sensing device. Analysis may comprise generating a QRS axis and a T axis value using the six leads I, II, III, aVR, aVL, and aVF as described herein.

Additionally, software incorporated with any of the systems, devices, methods described herein may determine a QRST angle by calculating the difference between the QRS axis and T axis as described herein.

Analysis may further comprise a rhythm analysis which may comprise determining a heart rate variability, a QT interval, or a corrected QT interval.

Additionally, software incorporated with any of the systems, devices, methods described herein may be used to determine a diagnosis or abnormality associated with an ECG. For example, as described an axis deviation may be associated with the abnormality of right or left ventricular hypertrophy. For example, heart rate variability may be associated with the diagnosis of atrial fibrillation. For example, QT interval changes may indicate certain arrhythmias.

Any of the systems, devices, and methods described herein may also be combined with sensors that measure physiologic parameters. For example, and of the systems, devices, or methods described herein may be incorporated with a blood pressure sensor. For example, any of the systems, devices, or methods described herein may be incorporated with a photoplethysmogram (PPG) sensor. For example, any of the systems, devices, or methods described herein may be incorporated with a temperature sensor. For example, any of the systems, devices, or methods described herein may be incorporated with a pulse oximetry sensor. For example, any of the systems, devices, or methods described herein may be incorporated with an accelerometer. Those having skill in the art will understand that other sensors that monitor or detect physiologic parameters are suitable for use with the systems, devices, and methods described herein.

In some embodiments, sensed physiologic data is transmitted to a processer in any of the systems, devices, and methods described herein. Software that is combined with any the systems, devices, and methods described herein may use said physiologic data that is sensed in combination with a sensed ECG to perform an analysis. For example, blood pressure data may be combined with ECG data by said software to provide an analysis that determines the presence of a ventricular tachycardia, an immediately life threatening condition.

The systems, devices, and methods described herein may include either or both of transmitters and receivers for transmitting and receiving wireless signals.

In some embodiments, software described herein also causes the transmission of a signal to a server when an abnormal analysis result is determined. For example, an abnormal analysis result comprises an abnormal ECG. For example, an abnormal analysis result comprises an abnormal QRS axis. For example, an abnormal analysis result comprises an abnormal QRST angle. In some embodiments, an abnormal analysis result comprises an abnormal ECG. For example, an abnormal analysis result comprises an abnormal heart rate variability value. Fr example, an abnormal analysis result comprises an abnormal physiologic parameter value. The transmitted signal may comprise a signal to an emergency care provider. For example, if an immediately life threatening condition is determined such as, for example, a VT the software described herein may send an emergency signal to a 911 operator, emergency care providers (e.g. paramedics), or other third party monitors.

In a fifth step, a six lead ECG is displayed on said display screen, said six lead ECG comprising said lead I, said lead II, said lead III, said lead aVR, said lead aVL, and said lead aVF.

While preferred embodiments of the systems, devices, and methods described herein have been shown and described herein, it will be obvious to those skilled in the art that such embodiments are provided by way of example only. Numerous variations, changes, and substitutions will now occur to those skilled in the art without departing from the user matter described herein. It should be understood that various alternatives to the embodiments of the systems, devices, and methods described herein may be employed in practicing the systems, devices, and methods described herein. It is intended that the following claims define the scope of the invention and that methods and structures within the scope of these claims and their equivalents be covered thereby.

In one embodiment, the method and systems describe herein may be combined with methods and systems for guiding and/or correcting placement of electrodes on a patient. These methods may be particularly useful for guiding placement of electrodes for ECG measurements. In general, the systems, devices and methods contemplated herein process a picture of a patient to output electrode positions on the patient. Typically, this may include presenting an image of the patient (e.g., a modified version of the picture of the patient) showing the locations for the electrodes relative to the actual patient picture.

For example, a system or device for guiding electrode placement as described herein may include control logic for controlling a processor (e.g., microprocessor of a computing device such as a hand-held computing device) to receive a picture of a patient, to analyze the patient to determine the correct placement of the electrodes, and to output an image of the patient on which the correct predetermined electrode positions have been marked. In general, the control logic may be configured as software, hardware or firmware, and may control a general-purpose computing device (e.g., computer, tablet, or the like) or a mobile telecommunications device (smartphone, such as iPhone®, Android®, etc.) to accept or acquire the picture and output the image of the patient. The processing step may be performed remotely or locally. In general, the processing step may include comparing the picture of the patient to a database (e.g., an electrode placement database) of various body types and corresponding predetermined, conventional or standard positions for electrodes associated with each body type. The picture of the patient may also be normalized prior to comparing the picture the patient database by adjusting the size, and/or in some cases the aspect ratio, brightness, contrast, or other image features, of the picture to allow direct comparison with the database. Normalization may be performed using a marker included as a part of the picture. For example, the picture of the patient may be taken with a marker of known or knowable size on the patient, and the marker may be used as a normalization marker to normalize the picture before comparison with the database. Normalization may also be performed to even out the brightness, contrast, sharpness, or other imaging quality of the picture. The marker may be placed or applied directly onto the patient (e.g., the patient's torso), e.g., by adhesive, etc.)

Also described contemplated are methods performed by the devices and systems for guiding electrode placement, such as methods of guiding electrode placement on a patient.

For example, contemplated herein are methods for guiding proper placement of electrodes on a patient that include: comparing a picture of the patient to an electrode placement database to determine positioning of electrodes on the patient, wherein the electrode placement database comprises representations of a plurality of body types and predetermined electrode placement positions corresponding to each body type; and presenting an image of the patient showing positions for electrodes on the image of the patient.

These methods may be particularly adapted for guiding placement of ECG electrodes on a patient in a standard or conventional configuration on the patient. Thus, the database may be configured to include a plurality of body types with corresponding conventional/standard electrode placement positions for each body type in the database.

In some variations electrode positions may be determined and indicated for all of the electrodes (e.g., all 10 electrode positions used for a standard 12 electrode lead). However, in some variations on a subset of the electrode positions may be determined and/or displayed. For example, a method of guiding positioning of a standard/conventional 12-lead electrode placement may determine and show only the six electrode positions on the patient's chest. In some variations where other electrode positions may be determined relative to one or more key electrode positions, only the position of the key electrode(s) may be shown.

In general, any appropriate picture of the subject may be used. In some variations, the system, devices or methods may include taking or acquiring the picture. In some variations, the picture may be taken by the system or device performing the method (e.g., a smartphone or other hand-held computer device). The systems, devices and methods described herein may instruct a user how to take the picture of the patient, including positioning the patient (facing forward, standing, sitting, lying, etc.), approximately how far from the patient to take the picture, positioning a normalization marker on or near the patient, and the like. The picture may be received as a digital image. The picture may include an image of the patient, and particularly a region of the patient's body to which the electrodes are to be applied. For example, when applying ECG electrodes, the picture may include the patient's torso or chest. Additional regions of the patient's body may be included, such as the patient's head, legs, etc. The patient may be standing, seated or lying down. The region of the patient to which the electrodes will be applied is typically bare (e.g., a may be shirtless or at least partially shirtless, so that the skin can be visualized). As mentioned, in some variations a normalization marker may be included as part of the picture. For example, a reference marker may be placed on the patient; the reference/normalization marker typically has a known or standard size, such as a coin (e.g., a U.S. quarter, penny, etc.). In some variations the reference marker is provided, and may be a distinct shape or color. In some variations the marker is automatically recognized by the apparatus. For example, the marker may include a readable code (e.g. bar code, alphanumeric code, QR code, etc.); alternatively, the apparatus may identify the marker by color, shape, etc.

In variations in which the method, system or device guides the user through taking or acquiring the picture, the picture may be qualified by the system or device. Qualifying the picture may include checking the picture to confirm that it is suitable and can be analyzed (e.g., compared) to the database.

As used herein the phrase "patient" is intended broadly to include any subject on whom the methods, devices and systems may be used to help position electrodes. A patient may include an animal (in systems and devices specifically configured for use with that type of animal) or human, and may include healthy or non-healthy subjects. As used herein a "user" may be a person using the systems, methods and devices as described herein. In some variations the user is the same as the patient, as the systems, devices and methods described herein may be used by a patient to guide placement of electrodes on his or herself.

In some variations, comparing the picture to the electrode placement database may comprise determining the standard placement of electrodes for a 12-lead ECG on the patient.

In general, comparing the picture of the patient to the electrode placement database may include determining a match (e.g., the closest match) between the picture and one or more representative body types in the patient database. Once one or more closely matching representative body types have been identified, the electrode placement corresponding to the representative body types for the match(s) may be mapped to the picture of the patient. Where more than one match is identified, electrode placement may be determined from the standard electrodes placements corresponding to the multiple representative body matches by weighting, averaging, or other appropriate statistical method for finding a consensus standard among the closest matches, and mapping this standard electrode placement to the picture of the patient.

As described in greater detail below, an electrode placement database typically includes a plurality (e.g., >10, >100, >1000, >10,000, etc.) of representations of standard/conventional electrode placement for different bodies. A representation of a body type may include an image of a body (e.g., picture, portion of a picture, etc.) or information extracted from an image of a body including electrode placement specific for that body, where the electrode placement has been confirmed or verified as within the standard/conventional bounds. The various body types may include body types of different shapes and sizes (height, weight, morphology), gender (male/female), age (infant, child, adult, elderly), physical morphology (shoulder width, chest size, waist size, etc.), and the like. Each body type representation may be unique, although similar body types may be included, creating clusters of body types around more common body types. All of the body types in the database may be pre-normalized to allow comparison between the different representations. Multiple different electrode placement databases may be used. For example, separate databases may be used for different patient positions (lying, sitting, standing, etc.), or for different patient genders, ages, etc. Further, different electrode placement databases may be used for different standard/conventional electrode placements.

Thus, in addition to normalizing the picture before comparing it to an electrode placement database, the picture may be processed to prepare it for comparison with the database. In variations in which the comparison is made by extracting features from the picture and comparing these extracted features to the representations of body types in the database, the extraction of features may be performed on the picture before (or as part of) the comparison. For example, when comparing the picture of the patient to the electrode placement database includes determining anatomical landmarks from the picture and comparing the anatomical landmarks to the electrode placement database, anatomical landmarks may be extracted from the picture first. The picture may also be processed to remove patient-identifying features (e.g., all or part of the patients face, etc.) which may be relevant to protect patient privacy As mentioned above, the comparison of the picture with the database may comprises interpolating between the closest matches to the picture and two or more representative body types in the patient database.

In some variations, comparing the picture of the patient to the database comprises using pattern recognition to determine the closest match between the picture and a representative body type in the database. In some variations, comparing the picture of the patient to the electrode placement database comprises comparing the normalized picture of the patient to the electrode placement database.

The methods, devices and systems contemplated herein may also include presenting the image of the patient showing positions for electrodes on the image of the patient. Any appropriate image of the patient may be presented, including a modified version of the picture of the patient showing the positions of the electrodes determined by comparison with the database. In some variations, the image of the patient is digitally displayed (e.g., on the handheld computing device). And may be enlarged (zoom in/out) or manipulated so that the user can see where to place the electrodes. In some variations the image may include additional guidelines, including measurements (rulers, distances in inches, mm, etc.) relative to the patient, including patient landmarks, such as anatomical landmarks, and/or relative to other electrodes.

The presentation of the image of the patient showing the conventional/standard position of the electrodes may show all of the electrodes, or some of the electrodes. In some variations, the presentation of the image may include a series of images separately showing the patient with different electrode positions indicated, to better allow a user to step through the process of applying or repositioning the electrodes. In general, the presentation of the image of the patient may be visual (showing the image) and may also include textual (written/spoken) instructions for applying the electrodes. For example, in variations of the systems and methods described herein intended for use with a handheld computer device, such as a smartphone, the device may be controlled to step the user through both taking the patient's picture and positioning (or repositioning) the electrodes by looking at the screen of the smartphone.

In some variations, the methods, devices and systems described herein may be used to correct and/or verify the position of electrodes already present on a patient. For example, the user may take or receive a picture of a patient with ECG electrodes already on the chest. Comparing the picture of the patient to the electrode-placement database may also compare the position of the electrodes already on the patient with the determined standard/conventional positions. Thus, comparing the picture of the patient to an electrode placement database may comprise comparing a picture of the patient having one or more electrodes already placed on the patient's chest to the electrode placement database. The position of the one or more electrodes already placed on the patient's chest may then be verified either automatically (indicating when one or more is incurred) or passively by overlying the correct positions (indicated in some specific way, e.g., by a color) onto the picture of the patient to form the presented image. In some variations the image presented includes an image of the patient showing corrected positioning of electrodes on the image of the patient.

Also contemplated herein are methods for guiding placement of ECG electrodes that include: receiving a picture of a patient including the patient's chest; comparing the picture of the patient to an electrode placement database to determine positioning of electrodes on the patient, wherein the electrode placement database comprises representations of a plurality of body types and predetermined conventional ECG electrode placement positions corresponding to each body type; and presenting an image of the patient showing positions for conventional ECG electrode positions on the image of the patient. The method of claim 17, wherein comparing the picture of the patient to the electrode placement database includes determining the closest match between the picture and a representative body type in the electrode placement database.

As mentioned above, comparing the picture of the patient to the electrode placement database includes determining anatomical landmarks from the picture and comparing the anatomical landmarks to the electrode placement database. In some variations, comparing the picture of the patient to the database comprises using pattern recognition to determine the closest match between the picture and a representative body type in the electrode placement database.

In any of the variations described herein, the comparing of the patient picture with the electrode placement database may be performed remotely from the other steps. For example, a smartphone may be used (e.g., using an application downloaded to the phone) to acquire the picture of the patient, and to present the image of the patient showing the conventional positions of the electrodes; the comparison of the picture with the database may be performed remotely, using a remote server. Thus, the database may be maintained separately from the application on the smartphone (or other device). This may allow modification, updating, or otherwise amending the database and/or the mechanisms for comparing the picture of the patient to the database. The image generated may then be presented on a handheld computer device after it receives information (or the generated image) back from the remote database. Alternatively, in some variations all of the steps are performed on the local level (e.g., using the handheld computing device, such as a smartphone or tablet computer).

As mentioned above, the picture of the patient may include a normalization marker. Thus the step of receiving the picture of a patient may include receiving a picture of a patient includes a normalization marker. In some variations, the picture of the patient received may include electrodes on the patient's chest; the method, device or system may verify the placement of the electrodes already on the chest relative to conventional ECG electrode placement positions.

Also described herein are methods for determining the placement of ECG electrodes including: receiving a picture showing a patient including and a normalization marker; normalizing the picture using the normalization marker; comparing the normalized picture to an electrode placement database comprising representations of a plurality of body types and predetermined ECG electrode placement positions for each body type to determine positioning of electrodes on the patient; and presenting an image of the patient showing positions for ECG electrodes on the image of the patient.

A system or device may be configured to perform any or all of the steps described above for receiving a picture of a patient including the region of the patient to which electrodes are to be applied, analyzing the picture, and providing an image of the patient (or any other patient-specific map) showing the location(s) of one or more electrodes on the patient based on predetermined, conventional and/or standard electrode positions Although many of the examples described herein are specific to systems, devices and methods of placing ECG electrodes (e.g., of a device 500) according to standard or convention 12-lead ECG electrode placement, these systems, devices and methods may be used (or adapted for use) with any predetermined, conventional and/or standard electrode positioning system, including electrodes for electroencephalograms (EEG), electromyogram (EMG), galvanic skin reflex (GSR), electrooculogram (EOG), bioimpedance (BI), etc. For example, the electrode placement database may include a variety of body types and corresponding predetermined, conventional and/or standard electrode positions for each of the body types for EEG, EMG, GSR, EOG, BI, etc. In some variations, the different electrode placement regimes (different conventional and/or standard electrode placement) may be linked in the database to each body type, and a user may select which placement regime to display. In other variations, more than one placement regime may be shown, either sequentially or simultaneously, for the same patient. For example, for ECG electrode placement, the electrode placement can correspond to 3-lead, 5-lead, and 12-lead ECGs.

A system for guiding electrode placement may generally include control logic, which may be executed as software, hardware, or firmware (or combinations thereof) that receive the picture of the patient, determine conventional and/or standard electrode placement for that patient using an electrode placement database, and output a map or image of the patient showing where on the patient the electrodes should be positioned. The system may also be configured to guide or walk the user through the process of taking the picture of the patient and/or positioning the electrodes on the patient. In some variations, the system is configured to guide the user by audible instructions, written instructions and/or visual instructions. The system may be configured to work from (e.g., control) a handheld computing device, including a smartphone to receive (and in some cases take) the picture of the patient and output the image of the patient with the determined electrode position(s) marked. For example, the system may be configured as an application for a smartphone that is downloadable onto the smartphone.

Any of the systems described herein may be dedicated systems that come pre-configured to receive a patient picture and output an image of the patient showing electrode placement positions, and do not require downloading of an application (e.g., software) onto a separate device. For example, a system may include a camera for taking a picture of the patient, control logic for receiving the picture, controlling analysis of the picture to determine electrode placement using an electrode placement database, and outputting a map or image of the patient showing the location of one or more electrodes according to a conventional and/or standard electrode positioning regime. The system may include all or a portion of the electrode placement database, or the system may communicate with a remote electrode placement database. Further, the system may include a comparison unit, which may include comparison logic for comparing the picture of the patient with the body types in the electrode placement database in order to find one or more close matches between the patient and the body types in the database, from which the predetermined conventional and/or standard electrode positions can be extrapolated to the patient picture.

The system may also be configured to use (and may include as part of the system) a normalization marker that is included in the picture of the patient. A normalization marker is typically a distinct maker that the systems/devices described herein may distinguish in the picture, and which may be used to provide scale and/or orientation for reference in the picture. For example, the normalization marker may be a sticker that can be attached to the skin of the patient; the sticker may be brightly colored, and may have a known size (e.g., an orange circle of one-inch diameter). The system/device can therefore distinguish this sizing marker in the picture, and can normalize the picture using the normalization marker. In some variations the normalization marker may also provide a reference position which the system may use in providing instructions for placement of the electrode(s). In some variation more than one sizing maker may be used. A normalization marker may be a common object of known dimension, such as a coin. The user may indicate in the system/device what the normalization marker (e.g., from a menu of possible normalization markers).

As mentioned, the image of the patient showing positioning of electrodes can be presented to the user on a handheld computer device. For example, the handheld computer device can be a mobile phone, smartphone, tablet computer, or camera with network connectivity.

Figure 6:
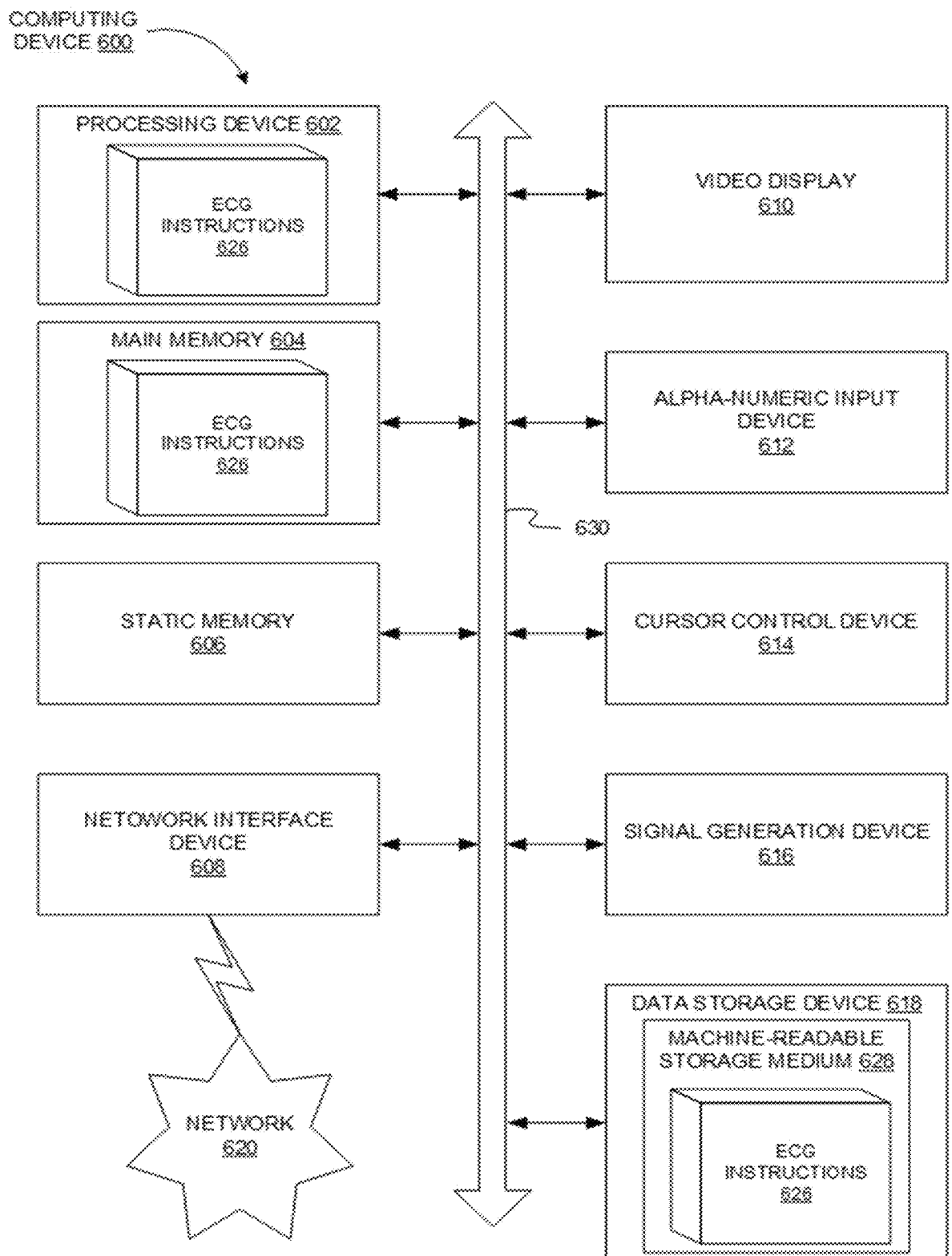
FIG. 6 is a block diagram of an example computing device that may perform one or more of the operations described herein, in accordance with some embodiments.

FIG. 6 is a block diagram of an example computing device 600 that may perform one or more of the operations described herein, in accordance with some embodiments. In various embodiments, computing device 600 may represent computing devices (e.g., servers) of the experimentation platform, third-party content provider client devices, and/or third-party content provider servers. Computing device 600 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include a processing device (e.g., a general purpose processor, a PLD, etc.) 602, a main memory 604 (e.g., synchronous dynamic random access memory (DRAM), read-only memory (ROM)), a static memory 606 (e.g., flash memory and a data storage device 618), which may communicate with each other via a bus 630.

Processing device 602 may be provided by one or more general-purpose processing devices such as a microprocessor, central processing unit, or the like. In an illustrative example, processing device 602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 602 may also comprise one or more special-purpose processing devices such as an application specific integrated circuit (ASIC), a field programmable gate array (FPGA), a digital signal processor (DSP), network processor, or the like. The processing device 602 may be configured to execute the operations described herein, in accordance with one or more aspects of the present disclosure, for performing the operations and steps discussed herein.

Computing device 600 may further include a network interface device 608 which may communicate with a network 620. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 616 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions 626, e.g., instructions for carrying out the operations described herein, in accordance with one or more aspects of the present disclosure. ECG instructions 626 may also reside, completely or at least partially, within main memory 604 and/or within processing device 602 during execution thereof by computing device 600, main memory 604 and processing device 602 also constituting computer-readable media. The instructions 626 may further be transmitted or received over a network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A mobile electrocardiogram (ECG) device comprising:
    an electrode assembly comprising electrodes, wherein the electrode assembly senses heart-related signals when in contact with a body of a user, and produces electrical signals representing the sensed heart-related signals;
    a converter assembly electrically connected to the electrode assembly, configured to convert the electrical signals to a modulated signal, wherein the modulated signal carries the electrical signals representing the sensed heart-related signals;
    a transmitter that transmits the modulated signal wirelessly to a computing device;
    a light-emitting device to provide ultra-violet (UV) light to illuminate a location on the body of the user where an electrode of the electrode assembly is to be placed; and
    a cylindrical housing containing the electrode assembly, the converter assembly, the transmitter, and the light-emitting device, and wherein a first electrode of the electrode assembly forms a ring that covers one end of the cylindrical housing, the first electrode comprising an opening through which the light-emitting device provides the UV light.

2. The mobile ECG device of claim 1, wherein the location on the body of the user corresponds to a precordial lead location on the body of the user.

3. The mobile ECG device of claim 1, wherein the location on the body of the user corresponds to an invisible marking on the body of the user.

4. The mobile ECG device of claim 3, wherein the invisible marking comprises a tattoo of invisible ink.

5. The mobile ECG device of claim 3, wherein the invisible marking comprises a temporary marking of invisible ink.

6. The mobile ECG device of claim 1, wherein the housing is a penlight form factor.

7. The mobile ECG device of claim 1, wherein the housing comprises a first male or female connector to snap-fit couple to a corresponding second male or female connector on a removable electrode.

8. A mobile electrocardiogram (ECG) system comprising:
    a penlight form factor, wherein the penlight form factor houses:
        an electrode assembly comprising electrodes positioned on an exterior surface of the penlight form factor, wherein the electrode assembly senses heart-related signals when in contact with a skin of a user, and produces electrical signals representing the sensed heart-related signals;
        an ultraviolet (UV) light-emitting device at an end of the penlight form factor, the UV light-emitting device to provide ultra-violet (UV) light to illuminate a location on the body of the user where an electrode of the electrode assembly is to be placed, wherein a first electrode of the electrode assembly forms a ring that covers one end of the penlight form factor, the first electrode comprising an opening through which the UV light-emitting device may provide the UV light;
        a converter assembly electrically connected to the electrode assembly, the converter assembly comprising a processor;
        a display electrically connected to the converter assembly, the display positioned on the exterior surface of the penlight form factor; and
        a memory comprising instructions to cause the processor to process the sensed heart-related signals and display the heart-related signals on the display.

9. The mobile ECG system of claim 8, wherein the location on the body of the user corresponds to a precordial lead location on the skin of the user.

10. The mobile ECG system of claim 8, wherein the location on the body of the user corresponds to an invisible marking on the skin of the user.

11. The mobile ECG system of claim 10, wherein the invisible marking comprises a tattoo of invisible ink.

12. The mobile ECG system of claim 10, wherein the invisible marking comprises a temporary marking of invisible ink.

13. The mobile ECG system of claim 8, the form factor further comprising a reservoir to store conductive gel and a button which when activated, causes an excretion of the conductive gel.

14. A method, comprising:
- activating, by a processor, a light-emitting device of a mobile electrocardiogram (ECG) device to illuminate an invisible marking on a body of a user using ultraviolet (UV) light, wherein the mobile ECG device comprises a first electrode that forms an opening through which the UV light may pass from the light-emitting device to the body of the user;
- determining where to place the first electrode of the mobile ECG device in view of the invisible marking revealed by the light-emitting device; and
- sensing heart-related signals when the electrode is in contact with the body of the user, and producing electrical signals representing the sensed heart-related signals.

15. The method of claim 14, wherein the invisible marking on the body of the user corresponds to a precordial lead location on the body of the user.

16. The method of claim 14, wherein the invisible marking comprises a tattoo of invisible ink.

17. The method of claim 14, wherein the invisible marking comprises a temporary marking of invisible ink.

18. The method of claim 14, wherein the mobile ECG device comprises a penlight form factor.

* * * * *